United States Patent [19]

Dasher et al.

[11] 4,297,098
[45] Oct. 27, 1981

[54] METHOD FOR GRADUAL COLORING OF HAIR TO A LIGHT BROWN SHADE AND PREPARATIONS FOR USE THEREIN

[75] Inventors: George F. Dasher, Inverness; Thomas J. Schamper, Chicago, both of Ill.

[73] Assignee: Alberto-Culver Company, Melrose Park, Ill.

[21] Appl. No.: 718,019

[22] Filed: Aug. 26, 1976

[51] Int. Cl.³ ............................................... A61K 7/13
[52] U.S. Cl. ......................................... 8/412; 8/416; 8/421; 8/424
[58] Field of Search ...................... 8/10, 2, 11, 32, 412

[56] References Cited

U.S. PATENT DOCUMENTS

| | | | |
|---|---|---|---|
| 3,337,411 | 8/1967 | Wilmsmann et al. | 8/10.2 |
| 3,415,608 | 12/1968 | Tucker | 8/10.2 |
| 3,694,138 | 9/1972 | Kalopissis et al. | 8/10.2 |
| 3,920,384 | 11/1975 | Feinland et al. | 8/10.2 |

FOREIGN PATENT DOCUMENTS

| | | | |
|---|---|---|---|
| 868325 | 5/1961 | United Kingdom | 8/10.2 |
| 983207 | 2/1965 | United Kingdom | 8/10.2 |

*Primary Examiner*—Natalie Trousof
*Assistant Examiner*—Vera C. Clarke

[57] ABSTRACT

Living human hair is progressively colored to the desired light brown shade by repeated applications of a preparation containing a low concentration of a mixture of oxidative dye components, namely, 2 to 3 components selected from p-phenylenediamine (or p-toluenediamine), pyrogallol, and m-aminophenol. To obtain a gradual, true color development, it is important to employ the dye components in certain relative proportions. In the use of the preparation, no oxidizing agent is added, and the color development reaction is obtained by contact of the dye mixture with atmospheric oxygen. The preparation is preferably in the form of an aqueous gel also containing hair grooming or conditioning agents.

4 Claims, 2 Drawing Figures

TERNARY DIAGRAM
(Percent by Weight)

METHOD FOR GRADUAL COLORING OF HAIR TO A LIGHT BROWN SHADE AND PREPARATIONS FOR USE THEREIN

BACKGROUND

The desirability of hair dye preparations which produce a gradual development of color has long been recognized. Metallic hair dyes have been used for this purpose, but are subject to limitations and disadvantages. Lead dyes are sold commercially for gradual coloring of hair. These use dilute solutions of a lead salt, such as lead acetate or nitrate, and also usually include elemental sulfur. The darkening of the hair is apparently caused by the formation of a complex molecule containing lead and sulfur, either chemically or physically bound to the hair. This system produces only one color—a slightly yellowish black. Brown shades cannot be obtained. Further, the blackish color is produced much more slowly than desirable for most users.

By employing direct dyes, such as nitro dyes, in sufficient dilution, gradual hair coloring can be achieved but it is difficult to control. Further, the user must be careful to avoid discoloration of the hands or skin by contact with the dyes, which have the full color at the time of application. Color produced by such direct dyes is also subject to the disadvantage that it will wash out on shampooing the hair.

The use of oxidative dyes for coloring human hair is also known. However, we are not aware that oxidative dye preparations have heretofore been employed for the gradual coloring of hair. In general, oxidative dye preparations consist of mixtures of ingredients which react in the presence of an oxidizing agent to produce a color. Such dye systems are described in the patent literature. (See, for example, U.S. Pat. Nos. 3,558,259, 3,630,655, 3,647,351 and 3,884,627.) Commonly, they utilize an aromatic diamine or an aromatic aminophenol, or both, in combination with a substituted or unsubstituted mono- or poly-phenol. These preparations are packaged and marketed under oxygen-free conditions and are mixed with an oxidizing agent, usually hydrogen peroxide, immediately prior to application to the hair. Color is thereby rapidly produced, so that the desired shade is normally achieved in a single application. In using and applying such oxidative dye preparations, it is necessary for the user to protect the hands and skin against discoloration.

It is known that oxidative dye preparations will develop color on exposure to atmospheric oxygen. However, as the color reactions occur, different shades or hues result, and the intermediate colors may be quite different than the final color. Consequently, if an attempt is made to use such a preparation for gradual coloration of human hair, such as by repeated applications, the user will have the problem of off-colors during the coloring process. If the treatment extends over several days or longer, as may be desirable, the lack of gradual true color formation would be a serious defect. It is believed that this may be the reason that no one heretofore has proposed the use of an oxidative dye for gradual coloration of human hair.

During the experimental work leading to the present invention, it was discovered that certain specific oxidative dye systems can be successfully employed for the gradual coloring of human hair to a light brown shade. To achieve the development of a gradual true color, with progressive deepening of the shade, it is necessary to utilize the dye components in certain relative proportions. There is no development of "off-color" at any time in the process, either during the actual treatments or in the "aging" periods between applications. The dye system, the required relative proportions, and the method of use will be described below in detail.

THE DRAWINGS

The accompanying drawings, comprising FIGS. 1 and 2, are ternary diagrams illustrating graphically the relative weight percentages of the components of the oxidative dye mixtures, which may be used in practicing this invention. These diagrams will also be further described below.

DETAILED DESCRIPTION

The oxidative dye components which may be used in practicing the present invention are: p-phenylenediamine (or p-toluenediamine), pyrogallol, and m-aminophenol. At least two and preferably three of these components are used in combination. More specifically, the dye mixtures which may be used in practicing the present invention, include:

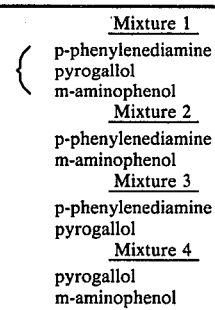

Mixture 1
p-phenylenediamine
pyrogallol
m-aminophenol

Mixture 2
p-phenylenediamine
m-aminophenol

Mixture 3
p-phenylenediamine
pyrogallol

Mixture 4
pyrogallol
m-aminophenol

In any of the foregoing Mixtures 1–3, part or all of the p-phenylenediamine may be replaced by p-toluenediamine. In general, p-phenylenediamine and p-toluenediamine for the purpose of this invention are equivalent when used on an equal molar basis.

For the purposes of the present invention, namely, the gradual progressive development of a light brown shade, it is important to employ the dye components in certain relative proportions. In general, on a weight percent basis, the proportions should be such that the dye mixture does not contain over 80% of any one of p-phenylenediamine, pyrogallol, and m-aminophenol, or an amount of p-toluenediamine greater than that equal to 80% of p-phenylenediamine on a molar equivalent basis. Advantageous formulations are those containing on a weight percent basis from 15 to 55% of p-phenylenediamine (or a molar equivalent amount of p-toluenediamine), from 0 to 30% of pyrogallol, and from 35 to 75% of m-aminophenol. One preferred formulation on a weight percent basis contains from 30 to 40% p-phenylenediamine, 1 to 10% pyrogallol, and from 55 to 65% of m-aminophenol. In a corresponding formulation, the 30 to 40% by weight of p-phenylenediamine is replaced by a molar equivalent amount of p-toluenediamine.

It has not been found necessary or desirable to include other oxidative dye components. However, small amounts (e.g. below 5%) of other oxidative dye components can be included for the purpose of toning or adjusting the light brown shade, providing said oxidative dye components do not produce off colors during the gradual color development. In general, it is preferred to use only the dye components listed above. Where toning or color adjusting is desired, this can be obtained by the incorporation of a small amount of a direct dye, such as Disperse Blue 1. The primary color producing reaction to give the light brown color should be due to the dye components listed above.

Figure 1:
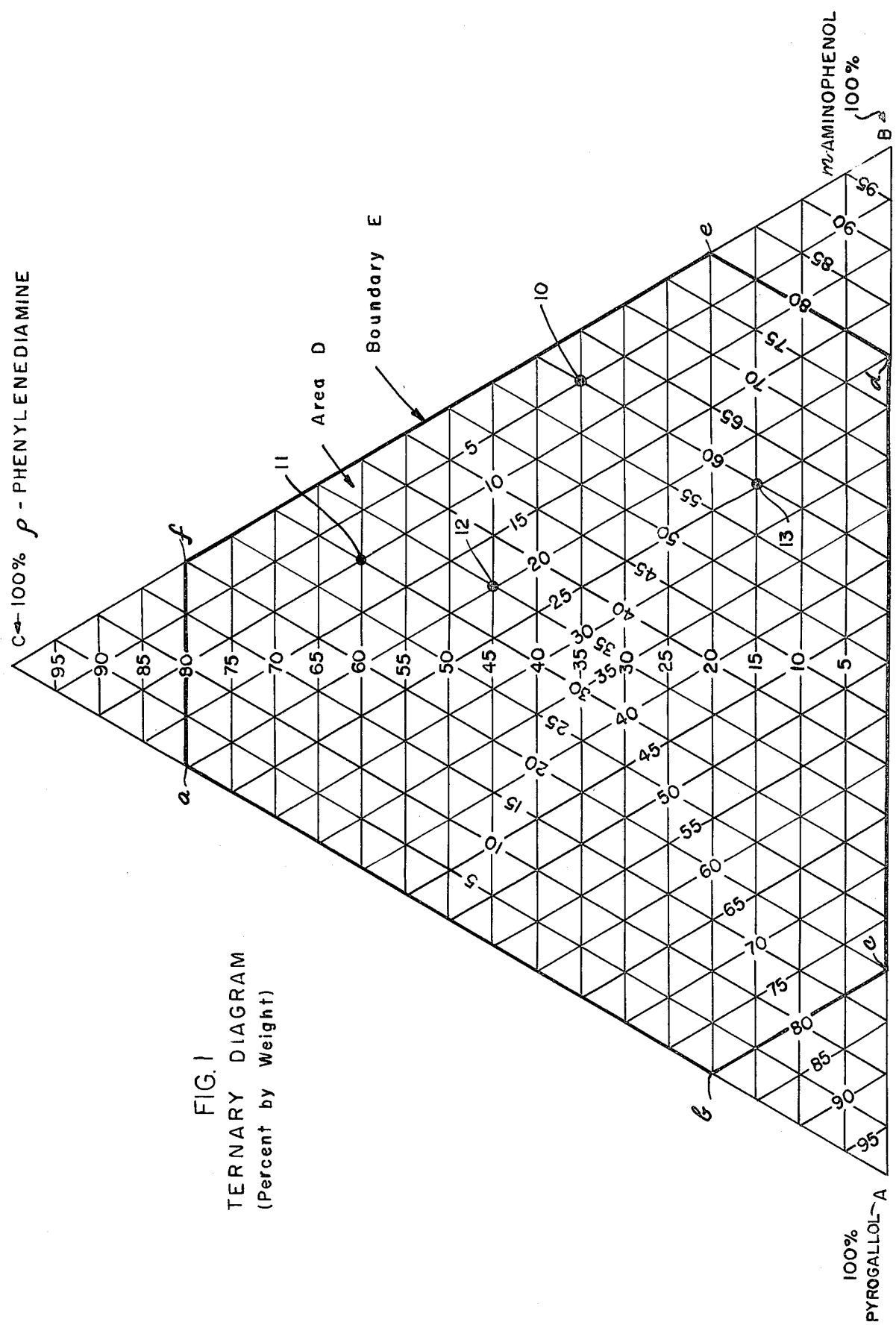
Figure 2:
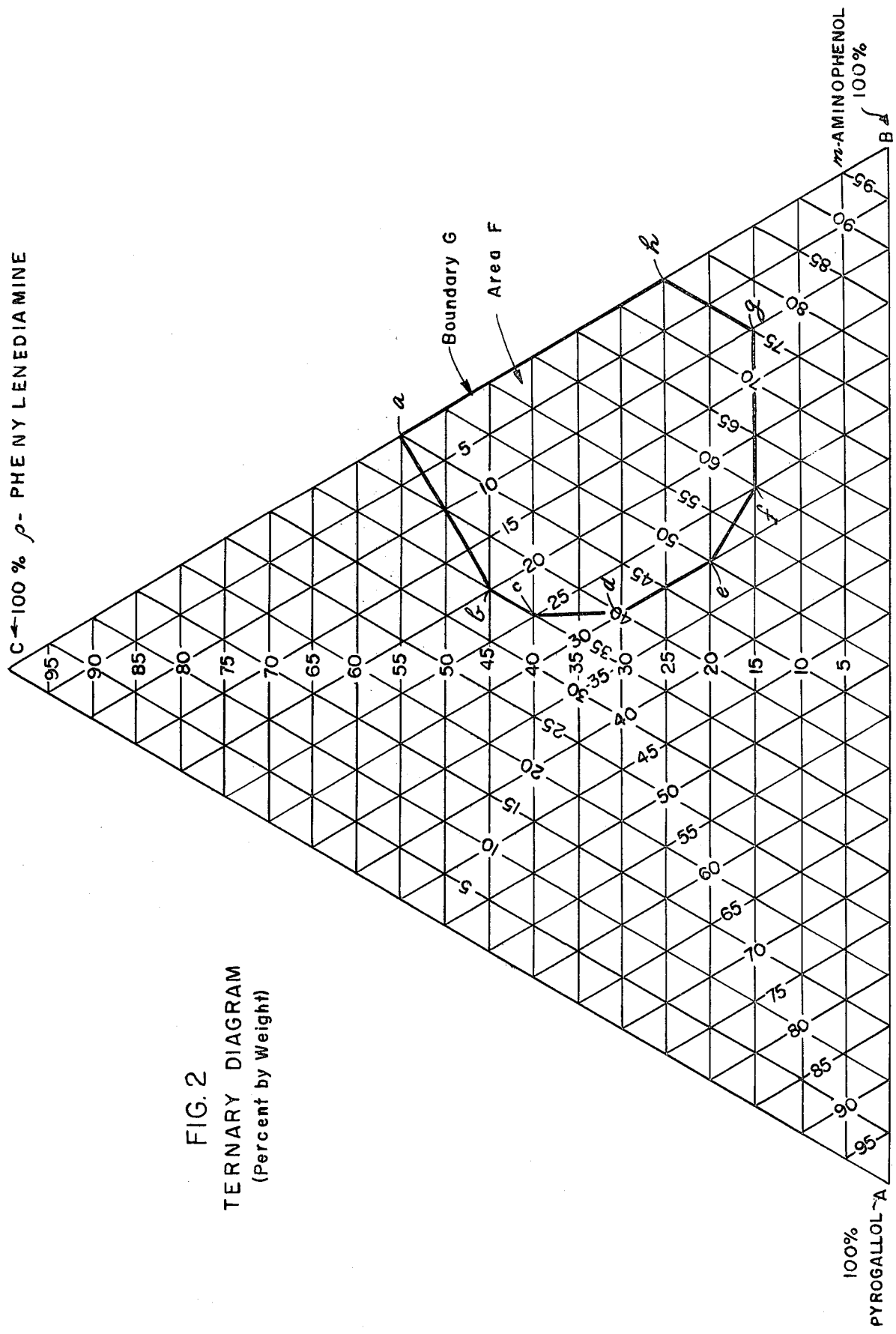

The relative proportions of the dye components usable in practicing the present invention can be determined from the ternary diagrams of FIGS. 1 and 2. In these diagrams, Apex A represents 100% pyrogallol; Apex B, 100% m-aminophenol; and Apex C, 100% p-phenylenediamine. The diagrams are scaled in weight percent units, the division lines representing increments of 5% (0, 5, 10%, etc.). It will be understood that any point on these diagrams defines the relative weight percents of the three components. The side A-B of the diagram represents formulations containing only pyrogallol and m-aminophenol; the side A-C, mixtures of pyrogallol and p-phenylenediamine alone; and side B-C, mixtures of m-aminophenol and p-phenylenediamine alone. The points within the borders of the diagram represent mixtures containing at least some of each of the three components.

Looking at FIG. 1, it can be seen that an area D is enclosed by a dark boundary line E. In general, formulations having value for the purpose of the present invention are those defined by falling on Boundary E or within Area D. The dark dots referenced by numbers 10, 11, 12, and 13 represent specific formulations as follows:

| | Formulations | | | |
|---|---|---|---|---|
| | Weight Percents | | | |
| | 10 | 11 | 12 | 13 |
| p-phenylenediamine | 35 | 60 | 45 | 15 |
| pyrogallol | 5 | 10 | 20 | 25 |
| m-aminophenol | 60 | 30 | 35 | 60 |

All of these dye mixtures produce light brown formulations. However, formulation 11 as compared with 10, produces a somewhat warmer light brown shade. The warmth of the brown shade increases in moving upwardly in the ternary diagram from point 10 to point 11. As compared with formulation 10, formulation 12 is yellower. In moving within the ternary diagram from point 10 to point 12, a progressively yellower light brown shade is obtained. Formulation 13 as compared with formulation 10 is a light brown shade which is ashier. In moving within the diagram from point 10 to point 13, the light brown shade becomes ashier. The difference between these shades is a matter of personal preference. They are all light brown shades, which develop in accordance with the method of the present invention.

For commercial purposes, it is believed that the most desirable formulations are those represented on FIG. 2, being dye mixtures defined by points within the Area F and including points falling on the Boundary G. This area is defined by straight lines extending between the points a-b, b-c, c-d, d-e, e-f, f-g, g-h, and h-a. The locating points are defined as follows:

| | Locating Points For Area F-FIG. 2 (Weight Percents) | | |
|---|---|---|---|
| Point | p-phenylenediamine | pyrogallol | m-aminophenol |
| a | 55 | 0 | 45 |
| b | 45 | 20 | 35 |
| c | 40 | 25 | 35 |
| d | 30 | 30 | 40 |
| e | 20 | 30 | 50 |
| f | 15 | 25 | 60 |
| g | 15 | 10 | 75 |
| h | 25 | 0 | 75 |

As previously indicated, in all of the above formulations p-phenylenediamine can be replaced on an equivalent molar basis with p-toluenediamine. It will be understood that ternary diagrams similar to FIGS. 1 and 2 could be replotted using Apex C as representing 100% p-toluenediamine. While the specific areas and boundaries corresponding to Area D and Boundary E of FIG. 1, and Area F and Boundary G of FIG. 2 will be different, the compositions defined by the diagrams will, in general, be equivalent.

The amine dye components, such as p-phenylenediamine, p-toluenediamine, and m-aminophenol, can be employed in the form of their salts as well as in their free base form. It will be understood that the weight proportions given above, the represented by the ternary diagrams of FIGS. 1 and 2 assume that the components are in their free base forms. When they are employed in a salt form, such as sulfates, chlorides, acetates, etc., it will be understood that this should be on a molar equivalent basis. Further, in determining relative proportions, the weight percents can be expressed in terms of the free base forms, although added in salt form.

For the purpose of the present invention, the dye mixtures are preferably combined to form a dilute solution or dispersion in an aqueous carrier. Small amounts of organic solvents may be included to improve the solubility of the dye components. For example, from 85 to 95% by weight of the preparations may be water, from 0 to 10% organic solvents, and from 0.1 to 0.6% of the dye mixture. In preferred formulations, the dye mixture is present in as little as 0.2 to 0.5% by weight. By employing the dye mixture in such low concentrations in the carrier, repeated applications of the preparation are needed to achieve a full color development. This is important to permit the gradual coloring of the hair to a light brown shade in accordance with this invention.

It is desirable to have the pH of the preparations on the alkaline side, such as a pH in the range of 7.5 to 10.5. Usually, a pH of 7.5 to 8.5 will be suitable. For adjustment of pH, if required, various alkalizing agents can be used. Where the formulation contains an alkyl amine, the pH may be adjusted with this reagent. For example, the pH can be adjusted with ethanolamine.

Since the preparation should be maintained free of oxygen (or any oxidizing agent) prior to application to the hair, it is desirable to employ water as the carrier which has been treated to remove dissolved oxygen. For example, boiled deionized water can be used.

It is also desirable to incorporate a small amount of an antioxidant, such as sodium sulfite in the preparations. The antioxidant helps protect the preparation from unintentional oxidation during packaging and shelf life. For the purpose of the present invention, the amount of antioxidant should be limited, so that when the preparation is in contact with air, atmospheric oxidation occurs readily. On application of the hair, it is desirable that complete atmospheric oxidation of the preparations occur within 30 to 60 minutes. In reference to sodium sulfite, this can be accomplished by incorporating from 0.01 to 0.03% by weight of sodium sulfite. Other antioxidants, such as thioglycolic acid, sodium hydrosulfite, ascorbic acid, etc. can be incorporated in equivalent concentrations.

In order that the preparations may also provide desirable hair grooming properties, hair conditioning and grooming agent may be incorporated as desired. These will normally be present in relatively small amounts, such as a total of from about 0.1 to 1% of the preparation. Suitable agents for this purpose include: proteins, mineral oil, polyvinylpyrrolidone, and derivatives of polyvinylpyrrolidone.

For convenience of use, the preparation may be in the form of an aqueous gel. Procedures for converting water solutions or dispersions to aqueous gels are well-known in the cosmetic arts. For example, the gel may be formed by reacting ethanolamine with polyacrylic acid, such as "Carbomer 940" (B. F. Goodrich Chemical Co., Cleveland, Ohio).

Suitable preservatives may also be included, such as methylparaben. Other preservatives that can be used are: ethylparaben, sodium benzoate, sodium o-phenylphenate.

It will also usually be desirable to incorporate a small amount of a perfume.

This invention is further illustrated by the following examples.

EXAMPLE 1

A preparation for gradual coloring of living human hair to a light brown shade is prepared according to the following formula.

FORMULA

| Ingredient | Description | Wt. % |
|---|---|---|
| 1 | water | 90.815 |
| 2 | Carbomer 940 | 0.37 |
| 3 | sodium sulfite | 0.02 |
| 4 | water | 2.00 |
| 5 | isopropyl alcohol | 4.50 |
| 6 | ethoxydiglycol | 0.50 |
| 7 | ethanolamine | 0.29 |
| 8 | methylparaben | 0.10 |
| 9 | p-phenylenediamine | 0.105 |
| 10 | pyrogallol | 0.015 |
| 11 | m-aminophenol | 0.18 |
| 12 | Disperse Blue 1 | 0.005 |
| 13 | Oleth-20 | 1.00 |
| 14 | perfume | 0.10 |

In the above formula the components are listed by their CTFA name as given in the CTFA Cosmetic Ingredient Dictionary (1973) and Bulletin (The Cosmetic, Toiletry and Fragrance Association, Inc., 1625 Eye Street, N.W., Washington, D.C. 20006). Oleth-20 is an ethoxylated oleyl alcohol supplied by Croda, Inc., New York, N.Y., under the trademark "VOLPO 20".

This formula produces an aqueous gel, which may be used as a hair grooming and conditioning aid, as well as for the gradual development of a light brown color. The pH of the product will be approximately 8.4.

One suitable manufacturing procedure is to introduce most of the water (Ingredient 1) into a tank equipped with an agitator. The agitator is started and Ingredient 2 (the Carbomer-940) is slowly added to avoid lumping. The batch is heated to 200° F. or above. As indicated above, the water has preferably previously been deionized. A stream of nitrogen is started to form a blanket over the batch at the time the tank is being cooled to room temperature. This nitrogen atmosphere is maintained at all times after the batch has been boiled, so that only nitrogen will redissolve in the batch. Ingredient 3 (the sodium sulfite) is then added.

In another smaller tank, the dye components and other components are combined. This tank must always have a stream of nitrogen flowing to maintain a nitrogen atmosphere. Ingredient 4 (water) and Ingredient 5 (isopropyl alcohol) are introduced into the second tank, and the tank is heated to 100° F. with stirring. Components 6 to 12 are added. Components 13 and 14 are separately mixed together, the Oleth-20 having been premelted, and the mixture is added to the tank containing the ingredients 4 to 12. When all of the dyes have been dissolved, the contents of the second tank are added to and mixed with the contents of the first tank. The contents of the first tank, comprising the Carbomer-phase, should have been stirring for at least an hour after cooling so that the Carbomer is well dispersed. After the two phases have been completely mixed, the product is transferred under nitrogen to a filling line.

The filling equipment should be designed so that a nitrogen atmosphere is always maintained in the areas where the product is exposed to the environment. The product is filled under a nitrogen atmosphere. For example, a shroud can be constructed over the filing heads and sealing components of the filling equipment, and a steady stream of nitrogen passed into the enclosed area. The filling tubes can be purged with nitrogen to eliminate oxygen.

The product can be packaged in suitable dispensing tubes, such as aluminum tubes with an internal epoxide resin coating. The container should not be permeable at atmospheric oxygen. Further, the dispensing tube should be designed so that there is no suck-back of air when the tube is squeezed and then released. Such a suck-back might cause the product in the neck of the tube to oxidize.

EXAMPLE 2

An aqueous gel product is prepared as described in Example 1, except that a molar equivalent amount of p-toluenediamine is substituted for the p-phenylenediamine. In the formula of Example 1, if p-toluenediamine is used in its free base form, the weight percent to be employed in the formula will be 0.119%.

EXAMPLE 3

The preparations of this invention, such as those of Examples 1 and 2, have particular utility for restoring a light brown color to light brown hair which has become partially gray. The product may be used by either men or women, but as formulated in Examples 1 and 2, it is probably best adapted for use by men as a complete grooming and conditioning aid, which also gradually produces the desired color effect. Preferably, the gel preparation is applied to clean, damp hair. For example, the hair may be washed, dried with a towel (towel dry but still damp), and then the preparation applied.

The preparation is used like a conventional paste-type hair dressing, but it is preferably not rubbed into the scalp. All the hair to be treated should be covered with the preparation. A comb can be run through the hair to assure even coverage. The hands of the user should be washed after the application, but because of the slow development of color, it will not be necessary to wear rubber gloves or otherwise protect the hands.

Following application of the preparation, the hair may be dried, as with a hair dryer. To prevent removal of the preparation while it is forming the color, it is preferable not to towel dry the hair again.

For each application, most of the color change will have occurred within 30 to 60 minutes. Some slight deepending of the color may continue to occur for up to 12 to 24 hours after the application. Very little total color change will be noted on the first application. Several applications will therefore be needed, such as once a day (24 hrs.) for 4 to 5 days or longer. At any time, when the proper light brown color shade is achieved, the user can discontinue the applications. The hair treated will be permanently colored, since the color produced does not wash out on shampooing. As the hair grows out, the treatments can be resumed to produce a similar color for the gray roots of the hair.

For the use of the preparations described, such as those of Examples 1 and 2, a natural light brown hair color can be achieved, while at the same time grooming and conditioning the hair. The conditioners and groomers in the preparation will leave the hair soft and natural. For most users, if the preparation is applied daily for 4 to 5 days, the gray will be eliminated and the hair will have the desired light brown color. The important point is that the color develops gradually and progressively, so that the progress is under the control of the user.

We claim:

1. A preparation for gradual coloring of living human hair to a light brown shade by air oxidation, comprising an aqueous carrier containing from 0.1 to 0.6 percent by weight based on the weight of the preparation of an oxidative dye combination, said dye combination consisting essentially of a mixture selected from the group consisting of (a) the mixture of p-phenylenediamine, pyrogallol, and m-aminophenol, and (b) the mixture of (a) in which p-toluenediamine is substituted on a molar equivalent basis for p-phenylenediamine, the said components of (a) being present in said mixture in the relative weight percents defined by the points within Area F of FIG. 2 including the points falling on Boundary G, or as further defined in (b) with respect to the substitution of p-toluendiamine for p-phenylenediamine, said preparation being free of oxygen prior to application to the hair and being capable of undergoing a progressive light brown color forming reaction on contact with atmospheric oxygen.

2. The preparation of claim 1 in which said mixture of dye components contains on a weight percent basis from 30 to 40% of p-phenylenediamine or corresponding molar equivalent amount of p-toluenediamine, from 1 to 10% of pyrogallol, and from 55 to 65% of m-aminophenol.

3. The method of gradual controlled coloring of living human hair to a light brown shade, comprising applying to the hair an oxygen-free preparation comprising an aqueous carrier containing from 0.1 to 0.6 percent by weight based on the weight of the preparation of an oxidative dye combination, said dye combination consisting essentially of a mixture selected from (a) the mixture of p-phenylenediamine, pyrogallol, and m-aminophenol, and (b) the mixture of (a) in which p-toluenediamine is substituted on a molar equivalent basis for p-phenylenediamine, the said components of (a) being present in the relative weight percents defined by the points within Area F of FIG. 2 including the points falling on Boundary G, or as further defined in (b) with respect to the substitution of p-toluenediamine for p-phenylenediamine, said preparation being free of oxygen prior to application to the hair and being capable of undergoing a light brown color forming reaction on contact with atmospheric oxygen, said preparation being applied a plurality of times in an effective amount with progressive development of the light brown color until the desired shade is achieved, the dye combination reacting to produce the color by contact with atmospheric oxygen.

4. The method of claim 3 in which said preparation of dye components contains on a weight percent basis from 30 to 40% of p-phenylenediamine or corresponding molar equivalent amount of p-toluenediamine; from 1 to 10% of pyrogallol, and from 55 to 65% of m-aminophenol.

* * * * *

UNITED STATES PATENT OFFICE
CERTIFICATE OF CORRECTION

Patent No. 4,297,098                    Dated October 27, 1981

Inventor(s) George F. Dasher, et al

It is certified that error appears in the above-identified patent and that said Letters Patent are hereby corrected as shown below:

On the title page, Item (75) Inventors should read:
-- Thomas J. Schamper, Chicago; Kathleen A. O'Cull, Northlake, [both] all of Ill. --.

Signed and Sealed this

Nineteenth Day of January 1982

[SEAL]

Attest:

GERALD J. MOSSINGHOFF

Attesting Officer

Commissioner of Patents and Trademarks